(12) United States Patent
Paisley (10) Patent No.: US 8,999,019 B2
(45) Date of Patent: Apr. 7, 2015

(54) PROCESS AND SYSTEM FOR GASIFICATION WITH IN-SITU TAR REMOVAL

(75) Inventor: Mark A. Paisley, Columbus, OH (US)

(73) Assignee: Taylor Biomass Energy, LLC, Montgomery, NY (US)

( * ) Notice: Subject to any disclaimer, the term of this patent is extended or adjusted under 35 U.S.C. 154(b) by 1496 days.

(21) Appl. No.: 12/091,038

(22) PCT Filed: Oct. 23, 2006

(86) PCT No.: PCT/US2006/041435
§ 371 (c)(1), (2), (4) Date: Apr. 21, 2008

(87) PCT Pub. No.: WO2007/048058
PCT Pub. Date: Apr. 26, 2007

(65) Prior Publication Data
US 2008/0244976 A1    Oct. 9, 2008

Related U.S. Application Data (60) Provisional application No. 60/728,989, filed on Oct. 21, 2005.

(51) Int. Cl.
*C10J 3/46* (2006.01)
*C07C 4/04* (2006.01)
(Continued)

(52) U.S. Cl.
CPC . *C07C 4/04* (2013.01); *C10J 3/482* (2013.01); *C10J 3/84* (2013.01); *C10J 2200/158* (2013.01); *C10J 2300/0916* (2013.01);
(Continued)

(58) Field of Classification Search
USPC ......... 48/210, 73, 77, 101, 111, 127.9, 127.1, 48/197 R, 61, 62 R, 209; 423/656, 652; 422/139
See application file for complete search history.

(56) References Cited

U.S. PATENT DOCUMENTS 3,736,111 A    5/1973   Gardner et al.
3,853,498 A    12/1974  Bailie
(Continued)

FOREIGN PATENT DOCUMENTS

DE    26 43 298     4/1978
EP    0628621 A2    12/1994
(Continued)

OTHER PUBLICATIONS

Israeli Office Action for Appln. Ser. No. 191075 mailed Jan. 8, 2012, 1 page—Hebrew, 1 page—English.
(Continued)

*Primary Examiner* — Kaity Handal
(74) *Attorney, Agent, or Firm* — Andrew F. Young, Esq.; Lackenbach Siegel, LLP (57) ABSTRACT

The present invention relates to a process and system for gasifying biomass or other carbonaceous feedstocks in an indirectly heated gasifier and provides a method for the elimination of condensable organic materials (tars) from the resulting product gas with an integrated tar removal step. More specifically, this tar removal step utilizes the circulating heat carrier to crack the organics and produce additional product gas. As a benefit of the above process, and because the heat carrier circulates through alternating steam and oxidizing zones in the process, deactivation of the cracking reactions is eliminated.

39 Claims, 6 Drawing Sheets (51) Int. Cl.
*C10J 3/48* (2006.01)
*C10J 3/84* (2006.01)
*C10K 3/00* (2006.01)
*C10K 3/04* (2006.01)

(52) U.S. Cl.
CPC . *C10J 2300/0983* (2013.01); *C10J 2300/1606* (2013.01); *C10J 2300/1637* (2013.01); *C10J 2300/165* (2013.01); C10K 3/008 (2013.01); *F23G 2201/301* (2013.01); *F23G 2201/304* (2013.01); *F23G 2201/40* (2013.01); *Y02E 20/16* (2013.01); C10K 3/04 (2013.01)

(56) References Cited

U.S. PATENT DOCUMENTS

| | | | | |
|---|---|---|---|---|
| 3,971,639 | A | * | 7/1976 | Matthews ........................ 48/202 |
| 4,157,245 | A | * | 6/1979 | Mitchell et al. ............ 48/197 R |
| 4,186,079 | A | * | 1/1980 | Roberts ......................... 208/127 |
| 4,264,435 | A | * | 4/1981 | Read et al. ..................... 208/129 |
| 4,298,453 | A | * | 11/1981 | Schoennagel et al. ........ 208/408 |
| 4,436,530 | A | * | 3/1984 | Child et al. ................. 48/197 R |
| 4,444,007 | A | * | 4/1984 | Mitchell et al. ................. 60/781 |
| 4,497,637 | A | * | 2/1985 | Purdy et al. ..................... 48/111 |
| 4,592,762 | A | | 6/1986 | Babu et al. |
| 4,828,581 | A | | 5/1989 | Feldman |
| 5,213,587 | A | | 5/1993 | Ekstroem et al. |
| 5,494,653 | A | | 2/1996 | Paisley |
| 5,922,090 | A | | 7/1999 | Fujimura et al. |
| 6,303,405 | B1 | | 10/2001 | Yoshida et al. |
| 6,426,512 | B1 | | 7/2002 | Ito et al. |
| 6,448,102 | B1 | | 9/2002 | Kneissl et al. |
| 6,460,472 | B1 | | 10/2002 | Silvennoinen |
| 6,530,978 | B2 | | 3/2003 | McQuigg et al. |
| 6,613,111 | B2 | | 9/2003 | Paisley |
| 6,649,437 | B1 | | 11/2003 | Yang et al. |
| 6,677,173 | B2 | | 1/2004 | Ota |
| 6,680,137 | B2 | | 1/2004 | Paisley |
| 6,808,543 | B2 | | 10/2004 | Paisley |
| 7,763,088 | B2 | | 7/2010 | Feldmann |
| 2001/0055324 | A1 | | 12/2001 | Ota |
| 2002/0137243 | A1 | | 9/2002 | Chen et al. |
| 2003/0140559 | A1 | * | 7/2003 | Krumm et al. .................... 48/77 |
| 2003/0189215 | A1 | | 10/2003 | Lee et al. |
| 2004/0045272 | A1 | | 3/2004 | Miyoshi et al. |
| 2004/0065889 | A1 | | 4/2004 | Ueda et al. |
| 2004/0110395 | A1 | | 6/2004 | Ueda et al. |
| 2004/0182003 | A1 | | 9/2004 | Bayle |
| 2004/0235210 | A1 | | 11/2004 | Tamura et al. |
| 2005/0098792 | A1 | | 5/2005 | Lee et al. |
| 2006/0099730 | A1 | | 5/2006 | Lee et al. |
| 2006/0151801 | A1 | | 7/2006 | Doan et al. |
| 2006/0154390 | A1 | | 7/2006 | Tran et al. |
| 2006/0154391 | A1 | | 7/2006 | Tran et al. |
| 2006/0154392 | A1 | | 7/2006 | Tran et al. |
| 2006/0154393 | A1 | | 7/2006 | Doan et al. |
| 2006/0157721 | A1 | | 7/2006 | Tran et al. |

FOREIGN PATENT DOCUMENTS

| | | |
|---|---|---|
| EP | 0953627 A1 | 11/1999 |
| JP | 05-291621 | 11/1993 |
| JP | 2000-277804 | 10/2000 |
| JP | 2001-049491 | 2/2001 |
| JP | 2001-313422 | 11/2001 |
| JP | 2003238973 | 8/2003 |
| JP | 2003-303743 | 10/2003 |
| JP | 2003-347590 | 12/2003 |
| JP | 2004-072052 | 3/2004 |
| JP | 2004-088083 | 3/2004 |
| JP | 2005-012188 | 1/2005 |
| JP | 5289055 | 6/2013 |
| RU | 2073064 C1 | 2/1997 |
| RU | 2346926 C2 | 4/2007 |
| TW | 540171 | 1/2003 |
| WO | WO 98/47985 A1 | 10/1998 |
| WO | WO 00/06671 A1 | 2/2000 |
| WO | WO 01/30943 A1 | 5/2001 |
| WO | WO2007/048058 | 4/2007 |

OTHER PUBLICATIONS

Office Action for Israel Patent Appln. Serial No. 191075 Mar. 23, 2012, 7 pages.
Office Action for Columbian Patent Appln. Serial No. 08-051.684 mailed Feb. 29, 2012, 5 pages.
Georgian National IP Search Report , Appln. No. AP2006010705 filed May 20, 2008, 3 pages.
Australian Office Action for AU Pat. Appln. No. 2006304867 dated Aug. 30, 2011, 2 pages.
New Zealand Examination Report for AU Appln. No. 567582 dated Jun. 20, 2011, 3 pages.
EPC Office Action for EPC Appln. No. 06817328.5 dated Jan. 21, 2011, 7 pages.
EPC Response to Office Action for EPC 06817328.5 dated Jun. 28, 2011, 25 pages.
"Steam-gasification of biomass in a fluidized-bed of olivine particles", by S. Rapagna, et al., Biomass & Bioenergy 19 (2000) pp. 187-197, 2000 Elsevier Science Ltd.
Letters Patent for Liberian granted Patent No. PCT/LR2008/00005 issued May 10, 2008, 1 page.
Ukraine Decision to Grant and Prosecution Materials for Ukraine Pat. Appln. Serial No. 200807037 filed Oct. 23, 2006 (Pat. No. 94919 issued Jun. 25, 2011), 68 pages.
Ueda, Tetsuzo, et al., "Vertical InGaN-based Blue Light Emitting Diode with Plated Metal Base Fabricated Using Laser Lift-Off Technique", Wiley—VCH Verlag-GmbH & Co., Phys. Stat. sol. (c) 0, No. 7, 2219-2222 (2003), 4 pages.
Li, W. H. , et al., "Electrochemical Deposition of Copper on Patterned $Cu/Ta(N)/SiO_2$ Surfaces for Super Filling of Sub-Micron Features", Journal of Applied Electrochemistry 31: 1395-1397 (2001), 3 pages.
Chu, Chen-Fu, et al., "Comparison of p-Side Down and p-Side Up GaN Light-Emitting Diodes Fabricated by Laser Lift-Off", Jpn. J. Appl. Phys. vol. 42 (2003) pp. L147-L150, Part 2, No. 2B, Feb. 15, 2003, 4 pages.
European Search Report dated Jan. 21, 2011 for Appln. No. EP 06 81 7328, 7 pages.
Examination Report and Notice of Acceptance of Complete Specification for New Zealand Pat. Appln. Serial No. 567582 mailed Dec. 14, 2011 (1 page).
Office Action for Australian Pat. Appln. Serial No. 2006304867 dated Jan. 10, 2012, 2 pages.
Japanese Pat. Appln. Serial No. 2008-536607, Amendments and Remarks filed Nov. 8, 2012, 8 pages—English, 12 pages—Japanese.
Japanese Pat. Appln. Serial No. 2008-536607, Notice of Reasons for Rejection mailed Dec. 4, 2012, 2 pages—English, 1 page—Japanese.
Malaysian Pat. Appln. No. PI 20081194, Substantive Examination Clear Report dated Feb. 15, 2013, 2 pages—English.
Response to Office Action for Israeli Patent Application Serial No. 191075 filed Jun. 24, 2012, 19 pages.
Notice of Acceptance for Australian Patent Appln. No. 2006304867 mailed Jul. 16, 2012, 8 pages.
Honduras Certificate of Registration No. 5197 issued Mar. 12, 2012, 1 page—Spanish.
Australian Certificate of Registration No. 2006304867 issued Nov. 8, 2012, 2 pages—English.
Canadian Appln. Serial No. 2,626,537, Office Action dated Nov. 7, 2012, 4 pages, English.
European Patent Application No. 06817328.5, Written Submission to European Patent Office filed Jan. 10, 2013, 38 pages.
Philippine Patent Application No. Jan. 2008-500938 Office Action mailed Mar. 4, 2013, 1 pages.
Taiwan Pat. Appln. No. 96139484, Notice of Allowance dated Apr. 22, 2013, 1 page—English; 2 pages—Chinese.
Taiwan Pat. Appln. No. 96139484, Allowed Claims, 8 pages—English.
Korean Pat. Appln. No. 10-2008-7011986, Office Action mailed Jun. 4, 2013, 6 pages—Korean, 5 pages—English.

(56) References Cited

OTHER PUBLICATIONS

Ukraine Decision of Grant for Appln. Serial No. 200807037 mailed Mar. 18, 2011, 7 pages, English translation, 8 pages.
Japanese Pat. Appln. No. 2008-536607, Notice of Allowance dated May 7, 2013, 1 page—English; 3 pages—Japanese.
Indian Pat. Appln. No. 3254/DELNP/2008, Office Action issued Mar. 23, 2013, 3 pages—English.
Taiwan Patent No. 1397580 granted Jun. 1, 2013, 1 page—English; 9 pages—Chinese.
Australian Divisional Pat. Appln. Serial No. 2012244230, Response to Office Action filed Jun. 14, 2013, 24 pages.
Canadian Application Serial No. 2,626,537 Office Action mailed May 13, 2014, 2 pages—English.
Verification of the Performance of Future Energy Resources' *SilvaGas* ® Biomass Gasifier—Operating Experience in the Vermont Gasifier, Paisley and Overend, 2002.
The Chemistry of Biomass Ashes in Pressurised Gasification, Maria Zevenhoven and Rainer Backman (Finnish University.
A Promising Power Option—The FERCO SilvaGas Biomass Gasification Process—Operating Experience at the Burlington Gasifier, M. Paisley, J.M. Irving and Ralph Overend, Jun. 4-7, 2001.
The *Silvagas*® Process From Future Energy Resources—A Commercialization Success, M. Paisley and Ralph Overend.
Winkleigh Biomass Electricity Generation Plant Description and Winkleigh PFD (from website).
Life Cycle Assessmen of a Biomass Gasification Combined-Cycle Power System, Margaret K. Mann & Pamela L. Spath of NREL, Dec. 1997.
Biomass Gasification Combined Cycle—DE-FC36-96GO10173 Agenda 2020, Weyerhaeuser—Presented to the Depart. Of Energy, Jul. 2000.
Peninsula Power Information (1) Peninsula Power Webpage Printouts (History, FAQs, Project Details and technology) (2) Revised Scope of EIA, Record of Consultation and Correspondence with Torridge District Council (3) Peninsula Power WINBEG 1—Likely Biomass Fuel Mix, Peninsula Power.
Biomass Gas & Electric Webpage Printouts; including SilvaGas powerpoint, BG & E. www.biggreenenergy.com.
Biomass Gasification Combined Cycle Opportunities Using the Future Energy *SilvaGas*® Gasifier Coupled to Alstom's Industrial Gas Turbines, Welch, 2003, Mark A. Paisley and Mike J., Jun. 16-19, 2003.
Observations on the Current Status of Biomass Gasification, Dr. Suresh P. Babu, May 2, 2005.
Preliminary Operating Results from the Battelle/FERCO Gasification Demonstration Plant in Burlington, Vermont, USA, FERCO, MP, MF, JW Black, JM Irving, R. Overend.
Conversion of Forest Residues to a Methane-Rich Gas in a High-Throughput Gasifier, Hermann Feldman, M. Paisley, H. Appelbaum, Dr. Taylor, Mar. 2, 1988.
Gasification of Refuse—Derived Fuel in a High Throughput Gasification System, Mark Paisley, Rober D. Litt, and Kurt S. Creamer, Jan. 29-Feb. 2, 1990.
Operation and Evaluation of an Indirectly Heated Biomass Gasifier Prepared for National Renewable Energy Laboratory U.S. Depaiiment of Energy (NREL), Battelle, Nov. 5, 1993.
Operation and Evaluation of an Indirectly Heated Biomass Gasifier Phase II—Task 1—Catalyst Screening Tests Prepared for NREL, Battelle, Feb. 16, 1995.
Biomass to Hydrogen Production Detailed Design and Economics Utilizing the Battelle Columbus Laboratory Indirectly Heated Gasifier, P. Spath; a. Aden; T. Eggeman; M. Ringer; B. Wallace and J. Jechura, May 2005.
Update of Hydrogen from Biomass—Determination of the Delivered Cost of Hydrogen, NREL, Apr. 2000.
Hot-Gas Conditioning of Biomass Derived Synthesis Gas, Mark Paisley and Robert D. Litt Battell, Aug. 30, 1993.
Conditioning and Detailed Analysis of Biomass Dervied Fuel Gas Ongoing and Planned Work by Battelle, Paisley, Anson and Ratcliff, Jun. 7, 1999.
Catalytic Conditioning of Synthesis Gas Produced by Biomass Gasification, Wang, Overend and Paisley.
Update of Hydrogen from Biomass—Determination of the Delivered Cost of Hydrogen, Spath, Mann and Amos—NREL, Dec. 2003.
Gas Cleanup for Combined Cycle Power Generation Using a Hot Gas Conditioning Catalyst, Paisley and Gebhard, Aug. 21, 1995.
Operation and Evaluation of an Indirectly Heated Biomass Gasifier Prepared for NREL, Battelle, Nov. 5, 1993.
Performance of the Dutch Chemical Industry and Society Based on Energy and Extended Exergy Accounting, Prof. dr. ir. F.J.J.G. (Janseen).
Catalytic removal of biomas tars; Olivine as prospective in-bed catalyst for fluidized-bed biomass gasifiers, Dutch Foundation for Research in Sustainable Energy, 2004.
"Formation, Decomposition and Cracking of Biomass Tars in Gasification" prepared by Technical University of Denmark—Dept. of Mechanical Engineering, Jan Fjellerup, Jesper Ahrenfeldt, Ulrik Henriksen, Benny Gobel Technical University of Denmark—Dept. of Mechanical Engineering, Apr. 2005.
Biomass Technology Group (BTG) Webpage Printouts www.gassifiers.com. 2002.
Comparison of Different Olivines for biomass steam gasification, R. Rauch; K. Bosch; H. Hofbauer; D. Swierczynski; C. Courson, A. Kiennerman.
The Influence of Fuel Composition on Agglomeration Behavior in Fluidised-Bed Combustion, H.J.M. Visser, Sep. 2004.
Electricity from Biomass, State-of-the-art co-firing and stand alone CHP Technology development in the Netherlands, H>J> Veringa, H. Boerrigter, J.H.A. Kiel.
Cost and Performance Analysis of Biomass—Based Integrated Gasification Combined-Cycle (BIGCC) Power Systems, NREL, Oct. 1996.
Biomass Gasification Overview, Richard Bain (NREL), Jan. 28, 2004.
New Bern Biomass to Energy Project; Phase I; Feasibility Study, NREL, Oct. 1995.
Gasification Technology and Advanced Biomass Gasification Projects, DOE/NREL.
Development and Commercialization of a Biomass Gasification/ Power Generation System; Second Biomass Conference of the Americas, Mark Paisley and Glenn Farris, Aug. 21, 1995.
FERCO Webpage Printouts www.fercoenterprises.com 2005 discussing operations in 1999 etc.
Emery Biomass Gasification Power System, Phillip, Hassett and Gatley, Nov. 27, 2002.
U.S. Dept. of Energy—Pittsburg Energy Technology Center Refilling and end Use Study of Coal Liquids, Aspen Process Flowsheet Simulation Model of a Battelle Biomass-Based Gasification Fischer-Tropsch Liquefaction and Combined-Cycle Power Plan, Bechtel, May 1998.
Environmental Assessment, Biomass Gasification Demonstration Project, Burlington, VT, DEO, Jun. 1995.
Equipment Design and Cost Estimation for Small Modular Biomass Systems, Synthesis Gas Cleanup, and Oxygen Separation Equipment Subcontract Report—NREL/SR-510-39945, NREL, May 2006.
Technical and Economic Assessment of Producing Hydrogen by Reforming Syngas from the Battelle Indirectly Heated Biomass Gasifier NREL/TP-431-8143, NREL, Margaret K. Mann, Aug. 1995.
The Battelle/FERCO Biomass Gasification Process Design, Engineering, Construction and Startup Process, Milton Farris, Mark Paisley, John Irving and Ralph P. Overend.
Commercial Demonstration of Atmospheric Medium BTU Fuel Gas Production from Biomass Without Oxygen, The Burlington, Vermont Project, John W. Rohrer, ZURN/NEPCO, Dec. 5, 1995.
Conference Report—Third Biomass Conference of the Americas, Dr. Stephen Schuck—Australian Biomass Taskforce Manager, Sep. 1997.
Future Energy Resources Corporation—Burlington Vermont Gasification Facility—Sample DCS Control Screens, Aug. 26, 1997.
Vermont Gasifier Project, Final Report—Phase I, Zern—NEPCO, Jul. 1995.

(56) References Cited

OTHER PUBLICATIONS

Integrated Gasification Combined Cycle and Steam Injection Gas Turbine Powered by Biomass Joint—Venture Evaluation NREL/TP 430-6080, NREL—Ralph Overend, May 1994.
Aspen Process Flowsheet Simulation Model of a Battelle Biomass Based Gasification, Fischer-Tropsch Liquefaction & Combined Cycle-Power Plant, Topical Report, Bechtel, May 1998.
Hydrogen Rich Biomass Steam Gasification, Study of Steam Reforming of Tolume as Tar Model Compound, Courson, Petit, Kiennermann.
Status of Biomass Gasification in Countries Participating in the IEA and GasNet Activity, Aug. 2004, Kwant and Knoef.
Ak-Chin Indian Community Biomass Feasiblity Study—Dept. of Energy, Office of Energy Efficiency and Renewable Energy, Oct. 20, 2004.
Biomass Feedstocks, NREL—Ralph Overend, Mark Davis, Rob Perlack, Tom Foust, Aug. 3, 2004.
Texaco Gasification Process—Innovative Technology Evaluation Report, National Risk Management Research Laboratory Office of Research and Development, Jul. 1995.
Hydrogen from Biomass State of the Art and Research Challenges IEA/H2/TR-02/001, NREL—Tom Milne; Carolyn Elam; Robert J. Evans.
Brighstar Environmental—Solid Waste and Energy Recycling Facility SWERF™, Brightstar Environmental.
Conversion Technology Evaluation Report Prepared for the County of Los Angeles, URS, Aug. 18, 2005.
Outlook for Advanced Biofuels, Carlo Hannelick.
Economic Evaluation of $CO_2$ Sequestrian Technologies Task 4, Biomass Gasification-Based Processing, DE-FC26-00NT40937, Rollins, Reardon, Nichols, Lee, Moore, Crim, Luttrell, Hughes, Apr. 2002.
Biomass and Black Liquor Gasifier/Gas Turbine Cogeneration at Pulp and Paper Mills, Eric Larson, Tom Kreutz and Stefano Consonni.
Energy from Poultry Litter, BTG.
Thermochemical Conversion of Forest Thinnings, Brian L. Polagye, 2005.
South West of England Regional Development Agency, Technical Review of the Winkleigh Biomass Electricity Generation Project, Nick Hall-Stride, Guy Turner, Jun. 2004.
Evaluation of Conversion Technology Processes and Products—Final Report—Integrated Waste Management Board of the State of California Including: Appendix A—Discussion of Thermochemical Process Definitions, Appendix B—Cover Letter and Survey Foini Sent to Vendors, Appendix C—List of Companies that Responded and . . . , Appendix D—Description of Pyrolysis Processes, Appendix E—Description of Combined Pyrolysis and Gasification Processes, Appendix F—Description of Gasification Processes, Appendix G—Description of Plasma Arc Processes from Survey Responses, Appendix H—Description of Biochemical Processes, Integrated Waste Management, Board of the State of California, Sep. 2004.
Gasification Technologies—A Primer for Engineers and Scientists, John Rezaiyan and Nicholas P., 2005.
Fluidization Engineering—$2^{nd}$ Edition, Daizo Kunii, Octave Levenspiel, 1991.
Primary Measurements to Reduce Tar Formation in Fluidize-bed Biomass Gasifiers, JHA Kiel, et al, Mach 2004.
The Chemistry of Coal Utilization, H.H. Lowrey, 1945.
International Search Report, PCT Office, Aug. 8, 2007.

* cited by examiner

PROCESS AND SYSTEM FOR GASIFICATION WITH IN-SITU TAR REMOVAL

CROSS REFERENCE TO RELATED APPLICATIONS

This application claims priority from U.S. Provisional App. Ser. No. 60/728,989, filed Oct. 21, 2005, the entire contents of which are herein incorporated by reference, and international application serial number PCT/US2006/041435 filed Oct. 23, 2006.

FIGURE SELECTED FOR PUBLICATION

FIG. 1

BACKGROUND OF THE INVENTION

1. Field of the Invention

The present invention relates to a process and system for gasifying biomass or other carbonaceous feedstocks in an indirectly heated gasifier and a method for the elimination of condensable organic materials (tars) from the resulting product gas with an integrated tar removal step. More specifically this integral tar removal step utilizes the circulating heat carrier to crack the organics and produce additional product gas. As a benefit of the above process and because the heat carrier circulates through alternating steam and oxidizing zones in the process, deactivation of the cracking reactions is eliminated.

2. Description of the Related Art

The related art involves a biomass gasification system and method as described in U.S. Pat. No. 6,808,543 (Paisley), the contents of which are incorporated herein fully by reference (also referred to as the FERCO system).

The '543 patent proves a gasification method involving a circulating fluidized bed (CFB) gasifier system wherein sand is used as a heat transfer medium. A first aspect of the system provides a method for reducing ash agglomeration in a parallel entrainment fluidized bed gasifier/combustion wherein Magnesium Oxide (MgO) is added into the thermal transfer material to alter a eutectic of the resultant ash and thereby raise a melting point of such ash to minimize agglomeration with the sand. In this way the '543 patent teaches the need to minimize sand+ash agglomeration through an increase of the ash melting point by adding MgO. Paisley '543 distinguishes itself from prior systems adding CaO and $Al_2O_3$ in attempts to reduce agglomeration by diluting ash.

The related art also involves a method for hot gas conditioning as described in U.S. Pat. No. 5,494,653 (Paisley), the contents of which are also incorporated herein fully by references.

The '653 patent discusses the production of a feed gas for hydrogen synthesis using gasification in a fluidized bed reactor (FBR), recirculating fluidized bed reactor (CFB), or in a fixed bed reactor (FB), and requires the use of a catalyst to adjust the hydrogen to carbon monoxide ratio in a water gas shift reaction, $$CO+H_2O=CO_2+H_2 \qquad \text{Equation 1}$$

in such a way as to not promote the formation of carbon, an undesired byproduct. Patent '653 teaches that alumina is a preferred catalyst and that conventional catalyst systems and methods for such reactions require the use of noble metals such as nickel, molybdenum, and the like, or of alkali materials such as potassium, sodium, and the like for catalysts. Further, conventional catalyst systems and methods do not suppress carbon to the extent desired in the '653 patent. Typical of these and other gas production operations are the following U.S. Pat. No. 233,861 to Jerzmanowski; U.S. Pat. No. 1,295,825 to Ellis; U.S. Pat. No. 1,875,923 to Harrison; U.S. Pat. No. 1,903,845 to Wilcox; U.S. Pat. No. 1,977,684 to Lucke; U.S. Pat. No. 1,992,909 to Davis; U.S. Pat. No. 2,405,395 to Bahlke et al; U.S. Pat. Nos. 2,546,606; 3,922,337 to Campbell et al; U.S. Pat. No. 4,726,913 to Brophy et al; U.S. Pat. No. 4,888,131 to Goetsch et al; U.S. Pat. No. 5,143,647 to Say et al; and British patent GB 461,402 (Feb. 16, 1937).

The '653 patent teaches a method of crackling and shifting a synthesis gas by providing a catalyst consisting essentially of alumina in an out-of-the-re-circulating-path chamber; and contacting the alumina catalyst with a substantially oxygen free synthesis gas of methane and/or higher molecular weight hydrocarbons; and water vapor at a temperature of about 530° C. to about 980° C., whereby methane and higher hydrocarbons are cracked according to the reaction, $$C_xH_{2y}+xH_2O=xCO+(1+y+x)H_2 \qquad \text{Equation 2}$$

and shifted by the reaction in Equation 1 (water gas shift reaction), whereby carbon formation is minimized at temperatures below 980° C.

As a consequence, the '653 patent teaches the use of alumina as a gas conditioning catalyst that can shift the so called water gas shift reaction to enable a ratio of $H_2$:CO of 2:1.

While the mechanical system in the '653 patent is generally similar to that in the '543 patent, a difference exists for the above-noted out-of-cycle (ex situ) lower temperature reaction chamber (maximum 815° C./1500° F.) that receives an output synthesis gas from the gasification module and contains the alumina catalyst for down-stream reaction. As a consequence, the '653 patent differs from that of the '543 system by providing both (i) an alumina ($Al_2O_3$) catalyst and (ii) providing that catalyst only in an ex situ chamber of low temperature that results in rapid downstream deactivation of the cracking reactions due to the deposition of carbon on the catalyst surface.

These related art references fail to appreciate a number of aspects noted in the present invention. These aspects include the use of a re-circulating heat transfer medium containing a catalyst, the removal of hydrocarbons (condensables) at high temperatures above about 370° C., and the removal of condensables in an in situ process (continuous removal with recycle).

As a consequence, a number of aspects of the present invention are not appreciated by the prior art. These include the ability of the present invention to recover heat to a significantly lower temperature following an in situ condensable removal step (due to the removal of tars from the gas at high temperature).

Similarly, the related art fails to appreciate the benefit of a separate gas-conditioning module that is heated in situ at high system temperatures (1000° C./1800° F.) by a thermal transfer medium heated in a combustor module and recycles for continuous use, thereby increasing the efficiency of all reactions due to higher temperature use.

Furthermore, the related art fails to appreciate the ability for increased hydrogen ($H_2$) recovery by including an in situ gas-conditioning module that operates at system high temperatures.

Finally, the related art in all cases fails to appreciate the use of steam in situ as a reactive to impact the water gas shift reaction in gas conditioning and thereby minimize the requirement for removal of condensables in a separate (ex situ) and costly downstream process Accordingly, there is a need for an improved process that enables removal of condensable products in situ and which therefore enables, but does not require, an improved energy recovery from product gas.

OBJECTS AND SUMMARY OF THE INVENTION

An object of the present invention is to provide a process for gasification with in-situ tar removal that responds to at least one of the needs noted above without a requirement of responding to more than one of the needs noted above.

The present invention relates to a process and system for gasifying biomass or other carbonaceous feed stocks in an indirectly heated gasifier and provides a method for the elimination of condensable organic materials (tars) from the resulting product gas with an integrated tar removal step. More specifically, this tar removal step utilizes the circulating heat carrier to crack the organics and produce additional product gas. As a benefit of the above process, and because the heat carrier circulates through alternating steam and oxidizing zones in the process, deactivation of the cracking reactions is eliminated.

Figure 1:
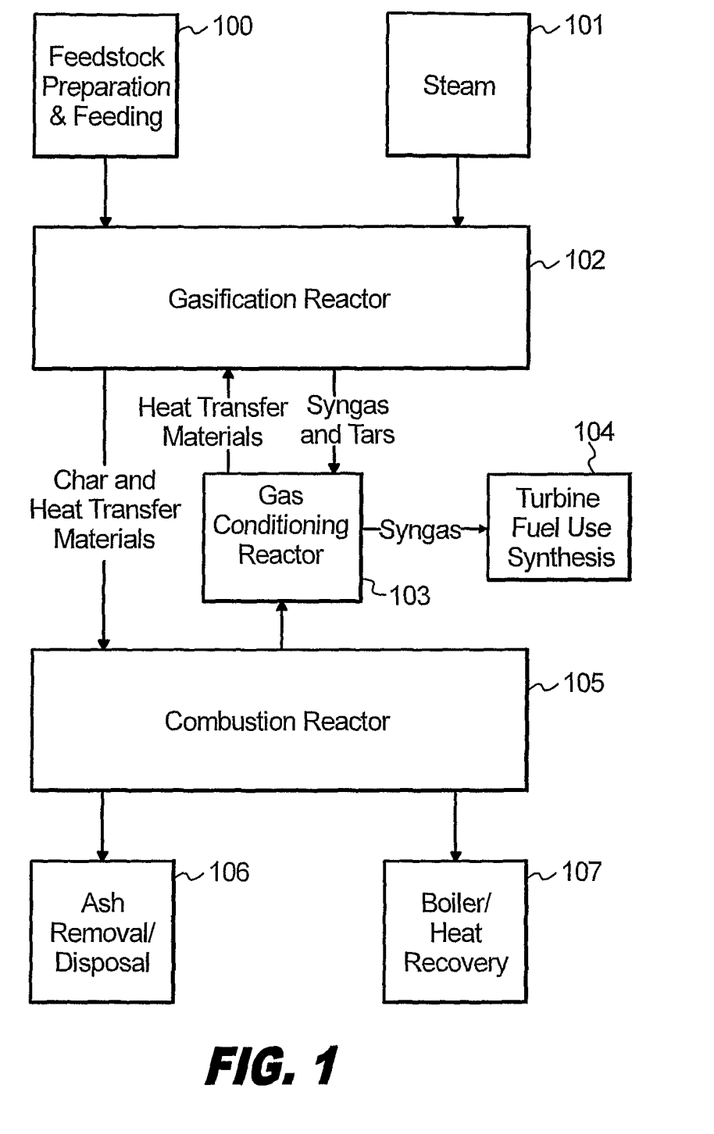
FIG. 1 is a pictographic flow diagram of the system according to the present invention.

Unlike other known biomass gasification processes, the presently provided process is not based on starved air combustion, but instead rather rapidly heats raw biomass in an air free environment to minimize tar formation and create a solid residue that is used as a heat source for the process. Significantly fewer emissions are produced in the process because of the relative ease of treating the high energy density, medium calorific value gaseous resultant product. In the process, biomass is indirectly heated using a heat transfer material (preferably sand) to produce a medium calorific value gas (approximately 17-19 $MJ/Nm^3$/350-450 Bti/scf) as shown in FIG. 1.

In the process a circulating heat transfer material is used to rapidly heat incoming biomass and convey unconverted material from the gasification reactor to an associated reactor. In the gasifier, heated heat transfer materials (sand) and steam contact the biomass. No air or oxygen is added so there are no combustion reactions taking place, providing an environmental advantage. The biomass is rapidly converted into medium calorific gas at a temperature of approximately 825° C. (Celsius). Any unconverted material along with the now cooled heat transfer materials (sand), pass through the gasifier and then are separated from the product gas.

The heat carrier materials and char formed in the gasifier are conveyed to the process combustor. In the combustor, air is introduced which in turn consumes the char in combustion and, in the process, reheats the heat carrier (sand) to approximately 1000° C. In the combustor all remaining carbon is consumed, resulting in substantially carbon-free ash suitable for environmentally friendly and inexpensive disposal. Due to the combustor conditions and the fact that the unconverted material is essentially carbon, emissions are desirably low from this step in the process. The reheated heat transfer solids are thereafter separated from the flue gas and returned to the gasifier. Ash is removed from the flue gas, resulting in a high temperature (approximately 1000° C.) clean gas stream, available for heat recovery.

The product gas exiting the gasifier is conveyed through a gas-conditioning reactor prior to final cleanup. In this cracking reactor, the product gas is heated to approximately 1000° C. (1832° F.), the temperature of the heat transfer material returning to the gasification reactor from the combustion reactor, noted above. At 1000° C., the condensable hydrocarbons (tars) are cracked to form lower molecular weight compounds such as hydrogen ($H_2$), Carbon Monoxide (CO), Benzene ($C_6H_6$), and Methane ($CH_4$). This cracking step eliminates higher molecular weight materials from the gas thus substantially simplifying downstream heat recovery and final gas clean up for particulate material. Furthermore, the present invention provides for the further production of increased hydrogen using the adjustment of the hydrogen: carbon monoxide ratio by an in situ water gas shift reaction as noted in Equation 1.

As an additional benefit of the present invention, by removing condensable from the product gas, enhanced heat recovery is possible. When condensables remain in the product gas, the product gas may only be cooled to approximately 370° C. during heat recovery. After condensable removal however, heat recovery may occur at least as low as 200° C. resulting in approximately a 40% improvement in recovered energy from the product gas.

By suitable selection of the circulating heat transfer materials, and the inclusion of a catalytically active material, the product gas may be further chemically adjusted providing water gas shift potential for (a) chemical synthesis, (b) hydrogen production applications or (c) adjusting chemical compositions for specific downstream uses.

According to one alternative aspect of the present invention, a method is provided for converting a synthesis gas containing hydrocarbons, the method comprising the steps of: providing both an indirectly heated gasification module for generating the synthesis gas from a carbonaceous fuel, and a combustion module for contributing to an operation temperature of the gasification module, providing an in situ gas conditioning module for receiving the synthesis gas from the gasification module and for operating at the operation temperature, and in the gas conditioning module, conditioning the synthesis gas to minimize a tar content therein.

According to another alternative aspect of the present invention, a system is provided for gasification with in-situ conditioning, comprising: a gasification module for gasifying a biomass feedstock into the synthesis gas, a gas conditioning module for receiving the synthesis gas from the gasification module and for conditioning the synthesis gas in an in situ circuit with the gasification module and a combustion module, and the combustion module for heating a thermal transfer material and for circulating the heated thermal transfer material to the gas conditioning module before circulating the thermal transfer materials to the gasification module.

According to another alternative aspect of the present invention, a system is provided for gasification with in-situ conditioning, the system comprising: an indirectly heated gasification module means for generating the synthesis gas from a carbonaceous fuel, and a combustion module means for contributing to an operation temperature of the gasification module, in situ gas conditioning module means for receiving the synthesis gas from the gasification module and for operating at the operation temperature, and in the gas conditioning module means, means for conditioning the synthesis gas to minimize a tar content therein.

According to another alternative aspect of the invention, an apparatus for conditioning a synthesis gas containing hydrocarbons, comprising: an indirectly heated gasification module for generating the synthesis gas from a carbonaceous fuel, and a combustion module means for contributing to an operation temperature of the gasification module, in situ gas conditioning module for receiving the synthesis gas from the gasification module and for operating at the operation temperature, and the conditioning module including a module for conditioning the synthesis gas to minimize a tar content therein comprising a system for cracking the hydrocarbons and shifting the synthesis gas, thereby producing a conditioned gas containing a hydrogen:carbon monoxide ratio having a positive hydrogen balance.

The above, and other objects, features and advantages of the present invention will become apparent from the following description read in conduction with the accompanying drawings, in which like reference numerals designate the same elements.

DETAILED DESCRIPTION OF THE PREFERRED EMBODIMENTS

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

Referring now to FIG. 1 a schematic flow process of the present system is provided for gasifying biomass or other carbonaceous feed stocks in an indirectly heated gasifier that eliminates condensable organic materials (hydrocarbons/tars) from the resulting product gas with an integrated tar removal step. More specifically, this tar removal step utilizes the circulating heat carrier to crack the organics and produce additional product gas in combination with a water gas shift reaction as will be discussed. As a benefit of the proposed process, and because the heat carrier circulates in situ through alternating steam and oxidizing zones in the process, deactivation of the cracking reactions is eliminated.

Unlike other known biomass gasification processes, the presently provided process is not based on starved air combustion, but instead rather rapidly heats raw biomass provided at a feedstock preparation and feed supply module 100 in an air free environment within a sealed gasification reactor 102 to minimize tar formation and create a solid residue (char) that is used as a heat source for the process within combustion reactor 105. Significantly fewer emissions are produced in the process because of the relative ease of treating the high energy density, medium calorific value gaseous resultant product. In the process, biomass is indirectly heated using a heat transfer material (preferably sand) to produce a medium calorific value gas (syngas) having approximately 17-19 $MJ/Nm^3$/350-450 Btu/scf from a gas-conditioning reactor 103 pulled for synthesis or turbine or fuel use at 104.

In the process (discussed in more detail in FIG. 2) circulating heat transfer material is used to rapidly heat incoming biomass and convey unconverted material from the gasification reactor to an associated reactor. In gasifier 102, heated heat transfer materials and steam 101 are contacted in a sealed system. No air or oxygen is added so there are no combustion reactions taking place, providing an environmental advantage. The biomass is rapidly converted into medium calorific gas at a temperature of approximately 825° C. (Celsius) or above. Any unconverted material (char) along with the now cooled heat transfer materials (sand), pass through the gasifier and then are separated from the product gas.

The heat carrier materials and char formed in the gasifier are conveyed to process combustor 105 for combustion and reheating. In the combustor 105, air is introduced which in turn consumes the char in combustion and, in the process, reheats the heat transfer carrier to approximately 1000° C. In combustor 105 all remaining carbon is consumed, resulting in substantially carbon-free ash suitable for environmentally friendly and inexpensive disposal at 106. Due to the combustor conditions and the fact that the unconverted material is essentially carbon, emissions are desirably low from this step in the process. The reheated heat transfer solids are thereafter separated from the flue gas and returned to the gasifier 102. Ash is removed from the flue gas, resulting in a high temperature (approximately 1000° C.) clean gas stream that may also be employed for a heat recovery process 107.

The product gas exiting the gasifier is conveyed through an in situ gas-conditioning reactor prior to final cleanup. In the gas conditioning reaction a cracking function occurs as the product gas is heated to approximately 1000° C. (1832° F.), the temperature of the heat transfer material returning to the gasification reactor from the combustion reactor, noted above. At 1000° C. (well above the related art references), the condensable hydrocarbons (tars) are reacted with steam inputs and cracked to form lower molecular weight compounds such as hydrogen ($H_2$), Carbon Monoxide (CO), Benzene ($C_6H_6$), and Methane ($CH_4$). This cracking step eliminates higher molecular weight materials from the gas thus substantially simplifying downstream heat recovery and final gas clean up for particulate material.

As an additional benefit of the present invention, by removing condensables from the product gas, enhanced heat recovery is possible without detrimental tar condensation. When condensables remain in the product gas, the product gas may only be cooled to approximately 370° C. during heat recovery. After condensable removal however, heat recovery may occur to at least as low as 200° C. resulting in approximately a 40% improvement in recovered energy from the product gas.

Figure 2:
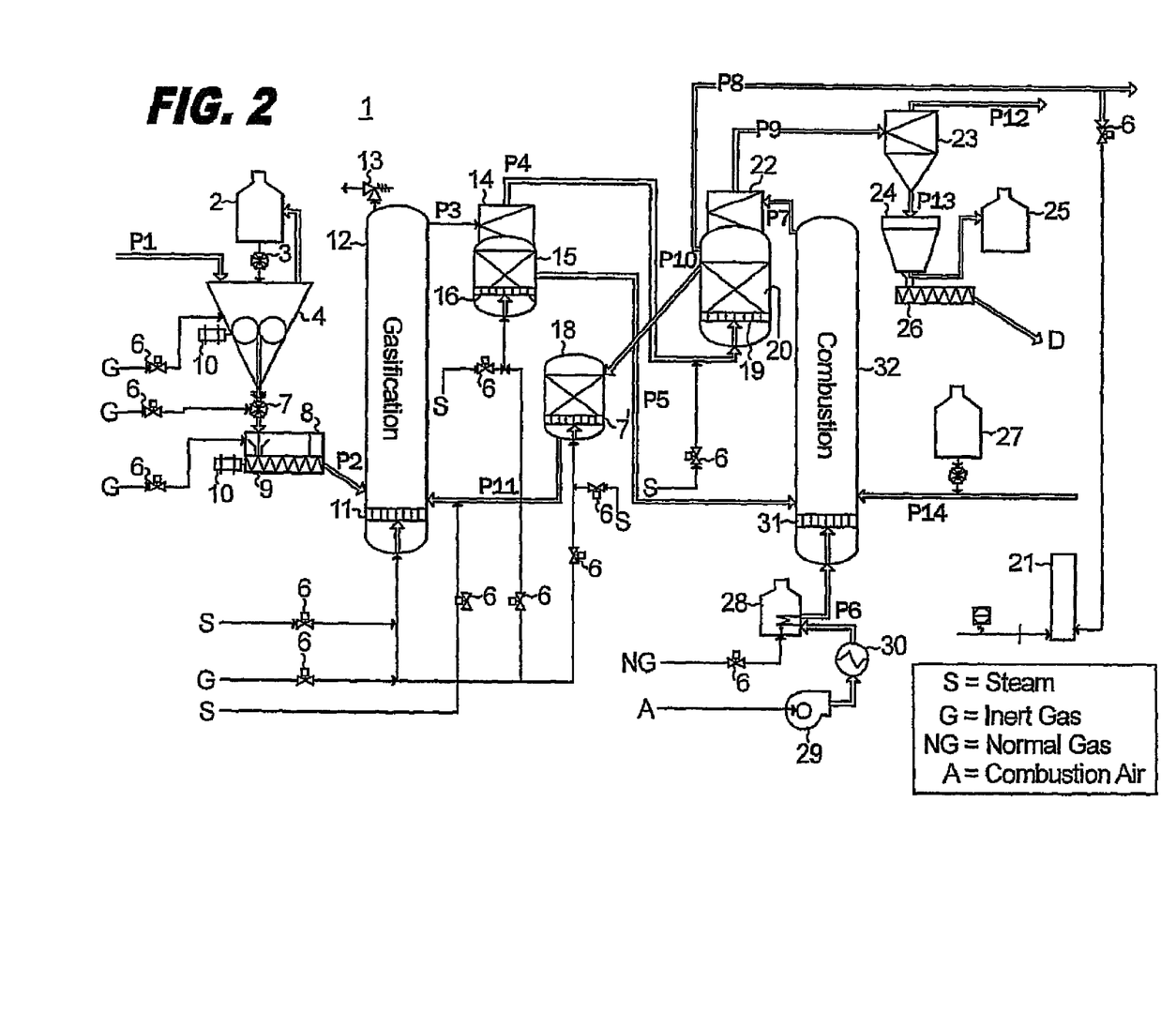
FIG. 2 is a detailed process flow diagram of one alternative and preferred embodiment of the present invention.

Referring now to FIG. 2 a more detailed gasifier system 1 is provided according to the present invention and generally includes a gasifier module 12 in fluid communication with a combustion module 32 which operate cooperatively to convert biomass inputted via process feed P1 into syngas, char, and heat.

Process feed P1 operates to condition and supply biomass feed stocks and includes a biomass fuel stream including commonly recognized biomass fuels such as construction and demolition materials, organic debris, and other biomass subject matter known to those of skill in the art. Biomass stream P1 is delivered into storage module 4 containing a feeding mechanism (as shown) driven by a motor 10 and input for an inert gas such as nitrogen or argon via valve 6.

A fugitive dust collector system 2 retains delivery fines and delivers the same to module 4 via rotary valve 3 or other mechanical means. The live storage module 4 delivers feed stock via rotary valve 7 supplied with inert gas via valve 6 to a fuel metering system 8 containing a screw conveyor 9 driven by a motor 10, as shown, and supplied with an inert gas via valve 6.

It should be recognized that biomass stream P1 may also contain a variety of precursor preparation modules including a moisture control module or dryer, storage bins modules, pre-combustors modules and/or chemical pre-treating modules as will be known to those of skill in the biomass preparation arts.

Process feed P2 delivers the prepared feed stock material to gasifier 12 which subjects the same to heat by contacting it with a heat transfer medium in an oxygen free environment, partially or wholly volatilizing the feed stock material to release a mixture of gasses including $H_2$, CO, $CO_2$, $CH_4$, $C_6H_6$ and other carbonaceous gases and tars as noted herein.

Gasification reactor or module 12 is heated via heating feed P11 with a hot heat transfer medium such as sand or other inert and/or chemically active solid material and gas fluidized material from combustion module 32 via a gas conditioning reactor 20, as will be discussed. Gasification module 12 can be of any conventional type known to those of skill in the art without limitation, such as a perforated plate type gas distributor used commonly in fluidized bed systems. As a consequence, gasification module 12 is shown with a distributor 11, and inputs of steam S via valve control 6 and an inert gas G also via a control valve 6. Gasification module 12 may be monitored via an access valve 13, as shown.

In the preferred embodiment noted steps are taken to ensure an entirety of the bed is fluidized thereby minimizing incomplete circulation and that the inner constructions of gasification module 12, combustion module 32, and related high temperature system components are constructed of a substantially non-reactive material.

Gasifier 12 operates as a circulating fluidized bed gasifier so that char formed during gasification retains the general geometric form of the feedstock and is circulated with syngas out an exit port via pathway 3 to gas conditioning reactor 20. Between pathway 3 and gas conditioning reactor 20 is an optional gasification reactor surge module 15 containing a reactor separator 14 (including a cyclone) and an associated fluidizing distributor 16 receiving inputs of steam and inert gas as shown to maintain flow. Separator 14 operates to separate sand and char directly to an input port of combustion module 32 via feed P5. As shown a syngas pathway P4 is shown noting the transfer of syngas from surge module 15 directly to an input on gas conditioning reactor 20.

Syngas pathway P4 is augmented with a steam input controlled by a control valve 6, as shown, and the syngas comprises at least CO and H2 as well as a variety of other gasses (and tars) in concentrations and combinations dependent upon the reaction within gasification reactor 12. As a consequence of the input of steam to gas conditioning reactor 20 there is truly a reaction occurring within this in situ module, here the water gas shift reaction and other reactions involving the cracking of petrochemical molecules.

Upon receiving syngas and tar flow via flow path P4 at operating temperature and distributed by a distributor 19, gas conditioning module 20 operates to crack the tars and balance the water shift reaction to create syngas (synthesis gas) containing Up to 50% $H_2$ and as little as about 0.0003 lb/cft (pounds per cubic foot) of residual tar both limits far exceeding the related references.

While not required by the present invention, conditioning reactor module 20 may further include an optional combustion reactor separation 22 for receiving ash and further non-convertible particles and transferring the same via a feed flow P9 to an ash separator 23 for distribution as flue gas via pathway P12 and as non-consumable ash via pathway P13 to an ash handling system 24 in operative communication with an ash dust collector 25 (for fines) and an ash collector 26 (for solids) for later distribution D.

In the preferred embodiment shown, an exit of combustion reactor 32 provides heated heat transfer materials via a flow path P7 to combustion reactor 22 and gas-conditioning module 20. As a consequence, gas-conditioning module 20 is maintained at high operation temperatures up to about 1000.degree. C. In the preferred embodiment shown, an additional surge module 18 receives heated heat transfer materials from gas conditioning module 20, ensures fluidization of the same with an inert gas feed via a flow valve 6 to a distributor 7', and may similarly receive a reactant such as steam via an additional flow valve 6, as shown.

Syngas that has completed conditioning in conditioning module 20 is removed via feed line P8 as product gas, as will be discussed.

As noted, feed flow P5 transports char and heat transfer materials to an input port of combustion module 32 for further combustion and reheating as necessary. Combustion module 32 receives heat via a distributor mechanism 31 from a natural gas combustion system, controlled by a valve 6 and combustion air supply A via a combustion blower 29 fed via a volume control 30 to a start up and maintenance heater 28 that combusts the natural gas and feeds the combined combustion gases via feed P6 to distributor 31 in combustion module 32. As a consequence of a combination of such a heat input via feed P6 together with the further combustion of the recovered char in combustion module 32 (thereby completing its reaction) the temperature of the heat transfer materials fed to gas conditioning module 20 via flow P7 is maintained and enhanced as needed for process control. After heating in gas conditioning module 20, heat transfer materials are transferred via flow P10 to gasification module 12 via surge module 18, as shown. Steam and inert gas may be passed to gasification module 12 via distributor mechanism 11, as shown.

Recognizing that heat transfer materials may need to be added to the continuously operating system, a heat transfer medium make-up module 27 operating via feed P14 may be operated to maintain or augment heat transfer materials and add catalyst materials as required by operators of system 1. Following entry of the same into combustion module 32 they are fluidized and join the fluidized flow materials within system 1 and exit the top of combustor 32 as flue gas.

Similarly, recognizing gas may not always be used downstream, and as an optional safety feature, following operation of gas conditioning module 20, system 1 includes an optional flare stack 21 accessible via a flow valve 6 from the exit flow P8 of product gas so as to provide a control combustion mechanism where the resultant syngas may not be otherwise employed downstream for materials manufacturing, fuel cell synthesis, fuel generation, and pre-use or pre-shipment storage.

As a consequence of the above discussion, the present disclosure shall recognize that the use of gasification reactor surge module 15, return surge module 18 and the associated pathways, distributors, and separators are optional to the present embodiment that requires only the use of gas conditioning reactor module 20. Similarly, without respective surge modules 15, 18, return flows P3/P4 may combine to directly supply exit heat transfer materials, syngas and tars from the exit port at the top of gasification module 12 to gas conditioning reactor 20 (in a flow similar to that shown in FIG. 1). In a related discussion, absent surge modules 15, 18, return heat transfer materials may return from an exit portal at the top of combustion module 32 through gas conditioning reactor 20 directly to an input portal in gasification reactor 12. As a consequence of the above paragraph, those of skill in the art will recognize that the flow process depicted in FIG. 1 is a preferred embodiment according to the present invention and that the detailed depiction in FIG. 2 is an additional (and optional) further preferred embodiment.

Figure 3:
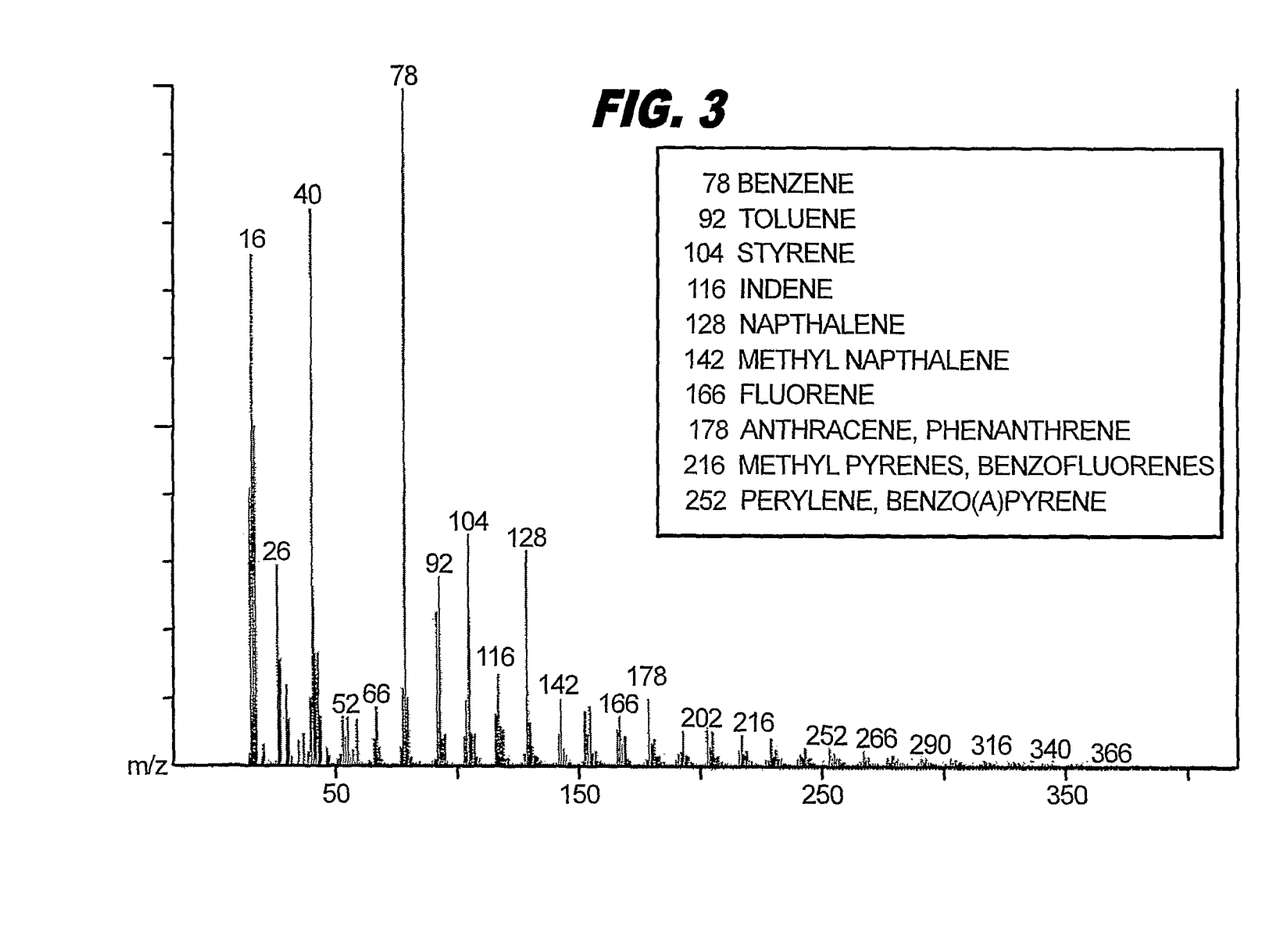
FIG. 3 is a graph of a Mass Spectrometry result showing the hydrocarbon analysis results before entering the gas-conditioning module of the present invention.
Figure 4:
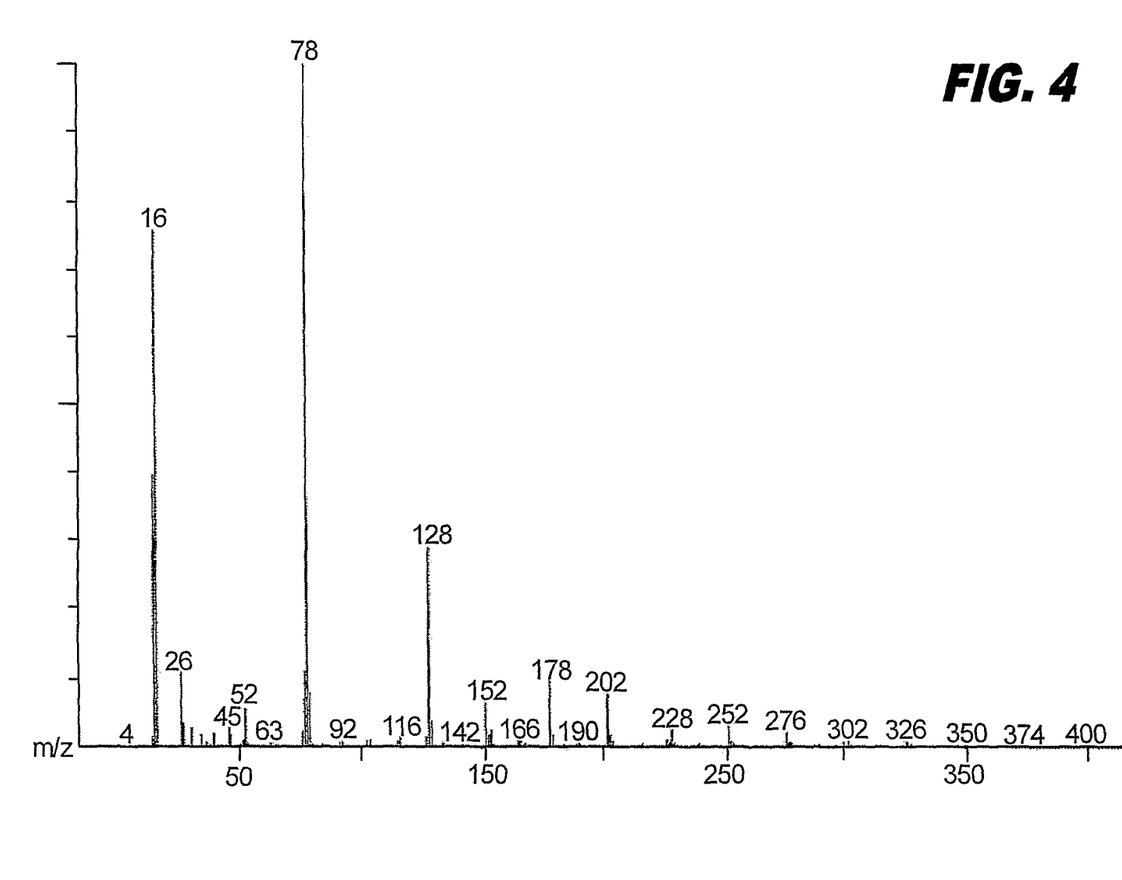
FIG. 4 is a graph of a Mass Spectrometry result showing the hydrocarbon analysis results of syngas upon exiting the gas-conditioning module of the present invention noting the substantive reducing of hydrocarbon.

Referring now to FIGS. 3 and 4, the present process flow diagram shown in FIG. 2 was tested by sampling the synthesis gas (resultant gas) from flow P3 exiting gasification module 12 and before entry of gas conditioning module 20 (shown as FIG. 3) and from flow P8 exiting gas conditioning module 20 (FIG. 4). Both are shown as Mass Spectrometry results with peaks noting the various hydrocarbon chains.

As will be obvious to those of skill in the art, FIG. 3 notes both a substantial volume of high molecular weight hydrocarbons (above the Benzene peak 78), and a high volume of lower molecular weight hydrocarbons (below the Benzene peak 78). Following gas conditioning in gas conditioning reactor 20, FIG. 4 notes the beneficial results of both reduced volume of total hydrocarbons of all molecular weights and the substantial shift of molecular weights to those hydrocarbons having generally lighter molecular weights (less than say the Benzene peak 78) that may be easily removed by downstream processes should any remain. As an additional benefit of the present invention, the post gas conditioning hydrocarbons are more predictably segmented and arranged and hence may be more readily retrieved by tailor-able downstream processes such as secondary ex situ elected solvent treatment, electrostatic precipitators, scrubbers, and other methods known to those of skill in the art.

As discussed herein, the preferred gasifier process system 1, includes an in situ gas conditioning module 20 operating at system temperature and producing significantly more hydrogen through the water gas shift reaction, $$CO + H_2O = CO_2 + H_2 \qquad \text{Equation 3}$$

due to the catalytic action of the heated solids in the gas conditioning reactor. Measured gas composition compared to other known gasification processes are shown below (dry basis) in Table I.

TABLE I

| | Gasifier | | | |
|---|---|---|---|---|
| Gas, Vol. % | Taylor[1] | FERCO[2] | FICFB[3] | Thermochem[4] |
| H2 | 43.8 | 20.7 | 37.7 | 52.2 |
| CO | 25.4 | 46 | 26.2 | 38.4 |
| CH4 | 10.7 | 15.6 | 9.9 | 1.8 |
| CO2 | 19.1 | 11.1 | 20.3 | 7.4 |
| C2H4 | 0.7 | 5.3 | 2.5 | 0.2 |
| C2H6 | 0 | 0.7 | 0.2 | 0.1 |
| N2 | 0.9 | 0.6 | 3.2 | 0 |

TABLE I-continued

| | Gasifier | | | |
|---|---|---|---|---|
| Gas, Vol. % | Taylor[1] | FERCO[2] | FICFB[3] | Thermochem[4] |
| Tars (lb/cft) pounds per cubic foot | ~0.0003 | 0.025 | 0.003 | Not reported in literature |

[1]From the system as shown
[2]From http://www.fercoenterprises.com for discussion of the FERCO-gasifier results
[3]From http://www.ficfb.at/ discussion of the FICFB-gasifier results
[4]From www.thermochem.net also discussion of the Kirk Othmer Encyclopedia of Chemical Technology Information, "Biomass Energy" by M. Paisley, pub John Wiley & Sons 2002.

As a consequence, to provide the water necessary for the water gas shift reaction, sufficient steam must be available in the gas entering the gas-conditioning step. This is accomplished by increasing the steam flow to the gasification module 20 (either via increasing the steam flow to the gasification module (an indirectly supply) or to the gas conditioning module via steam input to process flow P4 (a direct supply) or both). Graphically, the effect of the water gas shift is in the table at FIG. 5. As noted in the graph, "conversion" is defined as the decrease of a component in the gas, so a negative conversion indicates the formation of more of the component.

A major advantage of the gas conditioning reactor in the present invention is the substantive removal of the condensable hydrocarbons in the gasifier product gas in an in situ step without relying on complex downstream cracking steps. As shown above in Table I, significantly smaller quantities of these "tars" are present in the gas exiting the Taylor gasifier than are found in other indirectly heated gasifiers. This simplifies both final gas cleanup and heat recovery. The result is (1) a higher efficiency process as additional heat recovery is possible (to temperatures as low as 200° C.), and (2) a more economical process (as the costly removal of the condensables in a separate downstream process step is minimized or eliminated). It similarly should be noted that the nitrogen (N2) identified within the Taylor and Ferco systems is likely simply the result of minor purge nitrogen introduced initially into the stream. As a consequence, it is simple to contrast the poor results in Hydrogen ($H_2$) of the "Ferco system" with that of the system described herein (more than double). It should be similarly noted, that by adjusting the water gas shift reaction in the present in situ reaction system 1, the CO concentration may provide additional Hydrogen exceeding 50%.

As noted in the related art, a separate (ex situ), downstream catalyst reactor required for later hydrocarbon conversion depends on maintaining the catalyst activity at a high level so that the condensables can be cracked. At the temperature usually used for this (i.e. the gasifier temperature of 760° C./1400° F. to 816° C./1500° F.) this is materially difficult and costly as the cracking reactions tend to form free carbon, which subsequently deactivate the catalyst and slow the system requiring re-supply of fresh catalyst.

In the preferred configuration shown, the cracking reactions take place at a much higher temperatures (900° C./1652° F. to 1100° C./2012° F.) that is known in the related art and within the circulating system itself (in situ) thereby reducing the potential to form carbon. As a further advantage, by using the heat carrying/heat transfer medium as the in situ catalytic agent, any carbon that might form is consumed in the combustor module prior to being recycled to the gas conditioning reactor thereby further "regenerating" the material to maintain high catalyst activity levels.

Figure 6:
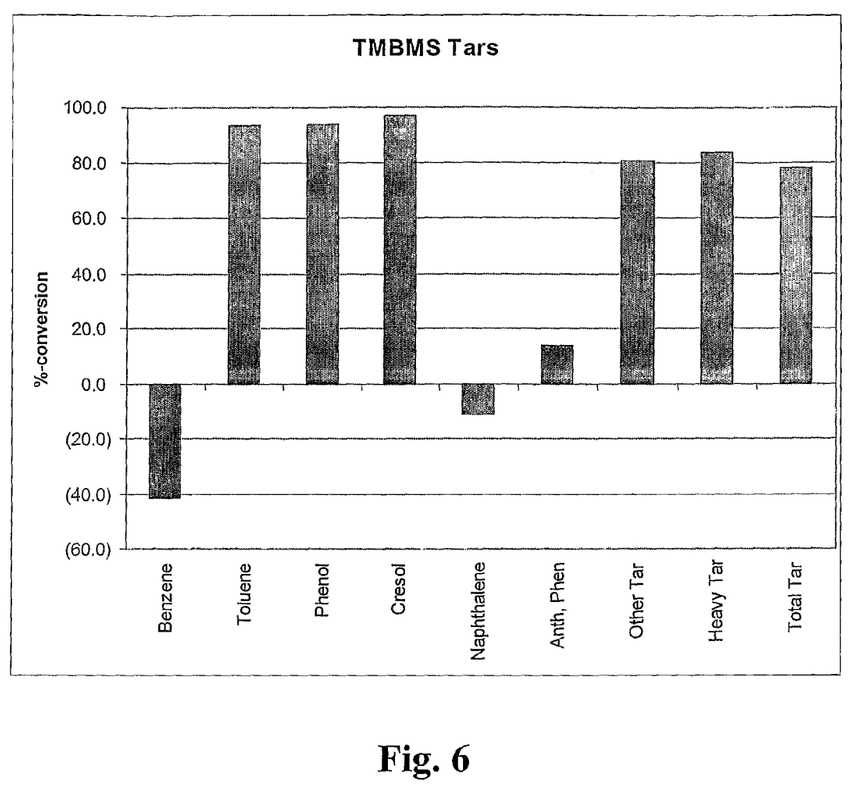
FIG. 6 is a graph representing the conversion of condensable hydrocarbons according to the present invention achieving over 95% conversion of some tars and 80% conversion of problem tars.

Referring now to FIG. 6, a figure illustrating the conversion of the condensable hydrocarbons occurring within the in situ gas conditioning reactor such that the conversion of total tar is nearly 80%, the conversion of so called heavy or high molecular weight tar exceeds 82%, the conversion of all other tars exceeds 80%, and the conversion of hydrocarbons (Toluene, Phenol, Cresol) exceeds 90% with a corresponding increase in the volume of benzene ($C_6H_6$) that may be readily addressed by known processes.

Figure 5:
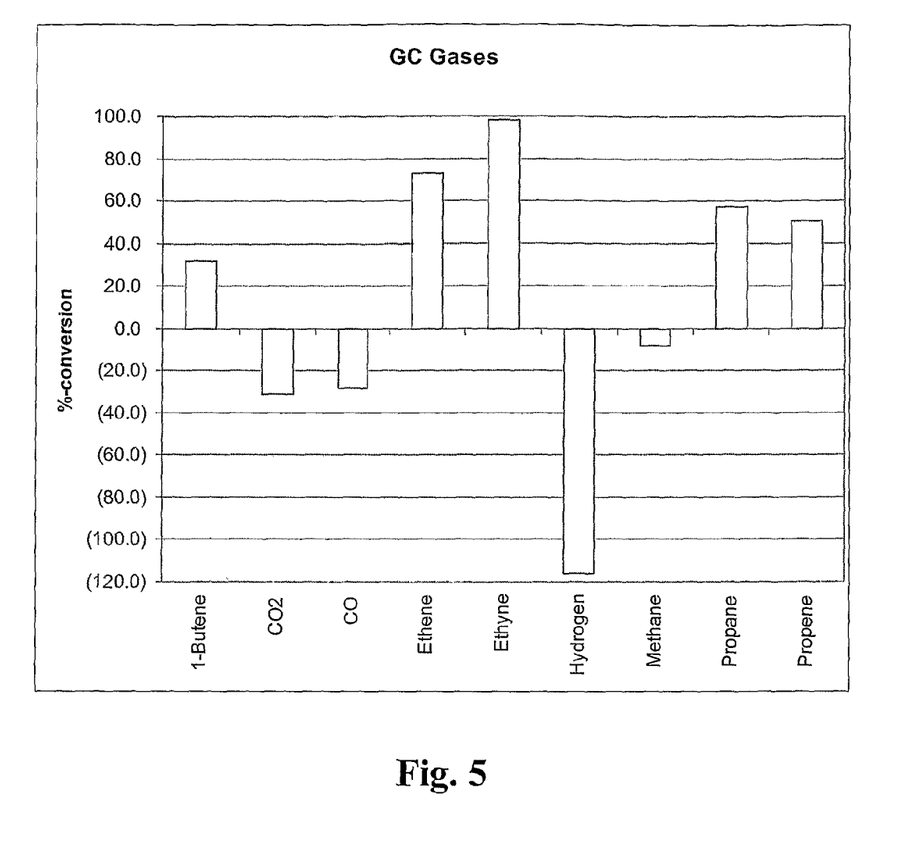
FIG. 5 is a graphical representation of the effect of the water gas shift in the present gas-conditioning reactor wherein the "negative" component (for hydrogen, $CO_2$, and CO) depicts the formation of more of the component and the "positive" component for the remaining hydrocarbons depicts their reduction.

In considering both FIGS. 5 and 6, those of skill in the art will consider the additional details shown below in Tables 2 and 3 to further support the present discussion. Specifically, table 2 below shows the detailed concentration data for the condensables, and table 3 shows the same data but expanded to provide detail for specific compounds.

TABLE 2

| | Results | | |
|---|---|---|---|
| Species | Inlet (mg/Nm$^3$) | Outlet (mg/Nm$^3$) | % conversion |
| Benzene | 7123 | 6703 | (41.3) |
| Toluene | 3596 | 158 | 93.4 |
| Phenol | 2376 | 99 | 93.7 |
| Cresol | 1206 | 26 | 96.7 |
| Naphthalene | 2105 | 1561 | (11.4) |
| Anth/Phen | 518 | 298 | 13.7 |
| Other Tar[1] | 12648 | 1632 | 80.6 |
| Heavy Tar[2] | 5775 | 623 | 83.8 |
| "Total Tar"[3] | 28223 | 4397 | 78.0 |

TABLE 3

| Molecular Weight | Formula | Chemical Name(s) | % conversion |
|---|---|---|---|
| 15, 16 | $CH_4$ | methane | (30.6) |
| 26 | $C_2H_2$ | acetylene | 58.3 |
| 78 | $C_6H_6$ | benzene | (41.3) |
| 91, 92 | $C_7H_8$ | toluene | 93.4 |
| 94 | $C_6H_6O$ | phenol | 93.7 |
| 104 | $C_8H_8$ | styrene | 93.4 |
| 106 | $C_8H_{10}$ | (m-, o-, p-) xylene | 97.3 |
| 108 | $C_7H_8O$ | (m-, o-, p-) cresol | 96.7 |
| 116 | $C_9H_8$ | indene | 93.8 |
| 118 | $C_9H_{10}$ | indan | 98.4 |
| 128 | $C_{10}H_8$ | naphthalene | (11.4) |
| 142 | $C_{11}H_{10}$ | (1-, 2-) methylnaphthalene | 97.1 |
| 152 | $C_{12}H_8$ | acenapthylene | 40.2 |
| 154 | $C_{12}H_{10}$ | acenaphthene | 72.3 |
| 166 | $C_{13}H_{10}$ | fluorene | 89.0 |
| 178 | $C_{14}H_{10}$ | anthracene, phenanthrene | 13.7 |
| 192 | $C_{15}H_{12}$ | (methyl-) anthracenes/phenanthrenes | 99.3 |
| 202 | $C_{16}H_{10}$ | pyrene/fluoranthene | (19.6) |
| 216 | $C_{17}H_{12}$ | methylpyrenes/benzofluorenes | 92.3 |
| 228 | $C_{18}H_{12}$ | chrysene, benz[a]anthracene, ... | 24.4 |
| 242 | $C_{19}H_{14}$ | methylchrysenes, ethylbenz[a]anthracenes | 90.5 |
| 252 | $C_{20}H_{12}$ | perylene, benzo[a]pyrene, | 16.7 |
| 266 | $C_{21}H_{14}$ | dibenz[a,kl]anthracene, | 92.7 |
| 278 | $C_{22}H_{14}$ | dibenz[a,h]anthracene, | 45.5 |

In considering the above, it will be noted that regeneration of the heat transfer material was tested by passing air through the material after several hours of operation (significantly longer exposure to the product gas than would be the case in expected normal operation). During normal operation, the solids would be recycled after approximately 8 to 15 minutes. Both cracking results and water gas shift results before and after regeneration were identical.

In the system of one of the preferred embodiments of the present invention, the biomass is contacted by the heat transfer material and hot gas, it is pyrolyzed (gasified) and an entrained region of heat transfer material, char and carbonaceous particles forms in the upper end of gasifier module 12. Entrained heat transfer materials circulate through the entrained biomass, char, and hot gases. As the carbonaceous particles pyrolyze, they generate gas forming a relatively higher velocity region above the fluidized bed.

As depicted and discussed, in system 1 pyrolized solids are removed from the top of combustion reactor 12 for transport to either gas conditioning module 20 or combustion module 32 following separation, and removed from the system by entrainment despite the low inlet gas velocities below the bed. This is made possible by the design of using a fluidized region, above which is an entrained region from which all bed particles including inerts and char are removed. Thus, entrainment occurs in part because of the gas generated in situ contributing significantly to the volume of gas moving through the reaction vessel for later conditioning in gas conditioning module 20, while avoiding destructive slugging.

The carbonaceous biomass materials fed to gasifier module 12 may achieve greater than 60% conversion of the available carbon upon a single pass through the gasifier system 1 due to the present invention's ability to operate at temperatures above 980° C. The remainder of the carbon is burned in combustion module 32 to generate heat for the pyrolysis reaction upon recycle. If other fuel is used in combustion module 32, then additional carbon can be converted in the gasifier module 12. With wet fuels, such as municipal waste, carbon conversions might vary upward or downward depending on the operating temperature of the gasifier module 12 and consequently the preferred embodiment provides a series of pre-feed conditioning (and drying) steps before feeding via flow P2.

The inlet gas fed to gasifier module 12 typically can be steam (as shown), recycled-product-gas and inert gases such as nitrogen, argon, and mixtures thereof. Preferred gases for the invention are steam and recycled-product-gas, and most preferably steam and inert gases.

In this invention entrained material exits the gasification module 12 near the top and is passed through (the product synthesis gas) to the gas-conditioning module 20, and the solids (the char, carbonaceous material, and heat transfer materials) are returned to the combustion reactor module 32 for combustion and heating respectively. All system solids are entrained except for unwanted tramp material such as scrap metal inadvertently introduced with the fuel feedstock, for which a separate cleanout provision may be needed.

The system of the present invention is versatile and could be combined with any type of combustor, fluidized, entrained, or non-fluidized, for heating the heat transfer material. The heat transfer material is heated by passage through an exothermic reaction zone of the combustion module 32 to add heat.

As a consequence of the above, those of skill in the art will recognized the improvements provided herein; which include the use of an in-situ gas conditioning module, the use of a re-circulating phase having a catalytic feature or operation in its process, the use of steam in a gas-conditioning module as a reactant, the operational resultant ratio of $H_2$:CO of about 2:1 or higher thereby minimizing a need for subsequent modification (positive ratio regarding hydrogen).

Finally, it is recognized that for the generation of free hydrogen ($H_2$) we are using in situ gas synthesis instead of some form of petrochemical reaction such as a subsequent water gas synthesis.

Beneficial products produced by the above described system include a gas with such a highly favorable Hydiogen:

Carbon Monoxide ratio that it may be useful as a gasoline additive, or in fuel-cell synthesis, or in power production typically for a combined cycle gas turbine power generation system.

As noted above, while the present system generates up to and above 50% hydrogen which may be used directly, subsequent steps for hydrogen recovery may be used and these may optionally include; the common membrane separation process based on partial pressure or a second level or later process water-gas shift reaction.

As used herein, the phrase inert material is understood to mean relatively inert (relatively non-reactive) as compared to the rapidly reactive carbonaceous material and may include heat transfer materials such as sand, limestone, and other calcites or oxides. As noted more fully, some of these heat transfer materials may not be relatively inert and may otherwise participate as reactants or catalytic agents, thus "relatively inert" is used as a comparison to the carbonaceous materials and is not used herein in a strict or pure qualitative chemical sense as commonly applied to the noble gases. For example, in coal gasification, limestone is useful as a means for capturing sulfur to reduce sulfate emissions and is thus active in cracking the tar in gasification reactor 12 and gas conditioning module 20, but as used herein shall be relatively inert.

While one benefit of the presently disclosed system is substantial minimization of agglomeration due to the high temperature operating conditions and in situ gas conditioning reactor 20, other useful materials may also be added to the gasifier feedstock to further improve system operation and further enhance the generation of ready-to-use end gases removed from gas conditioning reactor 20. For example, it has been found that the agglomeration of ash, sand, and char in gasifier system 1 can be further reduced by adding of magnesium oxide (MgO), Olivine, or other Fe-surface containing compositions to the in situ heat transfer materials and optionally the feedstock materials. Since the conventionally known agglomeration is generally a result of the partial-melting of the ash at high temperature condensation, minimizing such high temperature condensation and restricting the original creation provides substantive benefits. In prior systems, calcium oxide (CaO) and alumina ($Al_2O_3$) have been added in an attempt to reduce agglomeration of ex situ ash by diluting the ash, and the U.S. Pat. No. 6,808,543 (lacking any form of in situ gas conditioning module) teaches that the addition of MgO is even more effective to reduce agglomeration by reducing the eutectic of the ex situ ash mixture and hence raising the melting point to effectively reduce agglomeration at a weight percent or between 1% and 25% of the feedstock weight.

However, in contrast to the teachings of the '543 patent, any other related reference the present invention provides for the use of an in situ Olivine catalyst material within the range of 1-50% by weight of the heat transfer materials and even more preferably between 2% and 40% of a catalytically active material is added to the in situ heat transfer material to reduce aggregation (via origination prevention, conversion, and elimination) and promote catalysis in accordance with the present invention.

As used herein the phrases heat transfer medium or heat transfer materials shall not be viewed by those of skill in the art as being restricted to sand or olivine, but shall instead by considered to include all inorganic solids capable of at least temporarily resisting thermal breakdown at temperatures of up to 1100° C./2012° F. As a consequence, such heat transfer materials shall not be viewed exclusively as to the materials noted herein, but rather inclusively, and as such may include (without limitation or exclusion) catalytically active materials and non-catalytically active materials, common sand (quartz or otherwise), olivine, silica ($SiO_2$ or $SiO_4$), alumina ($Al_2O_3$), feldspar, and other metal oxides (including MgO, $CaO_x$, $ZnO_x$, $ZrO_x$, $TiO_x$, $B_2O_3$), and multiple combinations and compositions involving the same, including those that are partially or wholly stabilized, previously sintered or otherwise thermally prepared, and which may be naturally occurring or artificially formed.

Those of skill in the art shall consider as used herein catalytically active heat transfer materials shall be recognized as catalytically active materials and include, but not be limited to all of those heat transfer materials above that exhibit decomposition activity of hydrocarbons; including treated and untreated Dolomite and treated and untreated olivine, and alumina (both naturally occurring and artificially formed types, and either treated with calcination or other methods), alkali metal oxides, noble metal oxides, Ni-based compositions (including $Ni/Al_2O_3$, $NiCuMo/SiO_2$ or $SiO_4$—$Al_2O_3$), Mg-based oxides, Fe-based oxides, Ca-oxides, V-based oxides, Cr-based oxides, Co-oxides, Cu-oxides, Mo-oxides, calcined dolomites, magnesites, zeolites, and high-temperature oxide compositions containing elements of the above.

As used herein, the phrase iron transport catalyst shall be understood to include, but not be limited to, those catalytically active heat transfer material noted above that contain iron as well as other iron-containing ceramic materials and compositions, including natural and artificially formed olivine.

Similarly, as will be understood by those of skill in the art, the use of the phrase in situ shall be recognized and referring to as an in-process activity or a process, such as gas conditioning, that occurs in a circulating fluid path between a gasification reactor and a combustion reactor, and not as a separate external process beyond the system. For example here, gas conditioning module 20 is "in situ" because it receives thermal transfer materials from both combustion module and syngas from gasification module.

In the claims, means- or step-plus-function clauses are intended to cover the structures and reactions described or suggested herein as performing the recited function or reaction and not only structural and chemical equivalents but also equivalent structures and compositions. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures. In a similar manner, the phrase catalytically active materials include those materials functioning as catalysts.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A method for converting a synthesis gas containing hydrocarbons, the method comprising the steps of:
   providing both an indirectly heated gasification module for generating a synthesis gas and a condensable material from a carbonaceous fuel having contact with a catalytically active heat transfer material, and a combustion module for contributing to an operation temperature of said gasification module;

separating said synthesis gas and said condensable material from char and said catalytically active heat transfer material;

providing an in situ gas conditioning module for receiving said synthesis gas and said condensable material from said gasification module and for operating at said operation temperature;

providing said combustion module with said char and said catalytically active heat transfer material, said combustion module consuming said char to contribute to heating said catalytically active heat transfer material;

in said gas conditioning module, conditioning said synthesis gas and said condensable material by contacting with said catalytically active heat transfer material at said operation temperature to minimize a tar content therein;

providing steam to said gas conditioning module and said gasification module; and circulating said catalytically active heat transfer material from said gasification module to said combustion module to said gas conditioning module then to said gasification module.

2. The method according to claim 1, wherein said step of conditioning said synthesis gas in said gas conditioning module further comprises at least one of the steps of:

cracking said condensable material; and shifting said synthesis gas, thereby producing a conditioned gas containing a hydrogen:carbon monoxide ratio in a positive hydrogen balance.

3. The method according to claim 2, further comprising the steps of:

providing a heat transfer material containing at least a first portion by weight of said catalytically active heat transfer material.

4. The method according to claim 3, wherein said heat transfer material circulated from said combustion module is heated to maintain an operation temperature, wherein at least said step of contacting occurs at said operation temperature occurs in said conditioning module, and wherein said synthesis gas is generated from an input biomass material in said gasification module.

5. The method according to claim 4, wherein said operation temperature is between about 825° C. (1500° F.) to about 1100° C. (2012° F.).

6. The method according to claim 4, further comprising the step of:

heating said gas conditioning module with said heat transfer material from said combustion module thereby maintaining said gas conditioning module at said operation temperature.

7. The method according to claim 3, wherein catalytically active heat transfer material includes at least one material selected from the group consisting of olivine, calcites, metal oxides, and an iron containing high temperature catalytically active material.

8. The method according to claim 3, wherein said at least a first portion of said catalytically active heat transfer material is between about 50% to 100% by weight.

9. The method according to claim 3, wherein said at least a first portion of said catalytically active heat transfer material is between about 80% to 100% by weight.

10. The method according to claim 9, wherein said at least a first portion of said catalytically active heat transfer material is between about 90% to 100% by weight.

11. The method according to claim 2, further comprising the steps of:

providing a steam supply to both said gas conditioning module and said gasification module.

12. The method according to claim 11, wherein said steam supply is provided to said gasification module in a velocity range of between about 0.50 ft/sec to about 15 ft/sec.

13. The method according to claim 12, wherein said steam supply is provided to said gasification module in a velocity range of between about 0.50 ft/sec to about 10 ft/sec.

14. The method according to claim 2, wherein said shifting said synthesis gas is increased by adjusting an amount of said provided steam.

15. The method according to claim 2, wherein said shifting said synthesis gas is increased by adjusting an amount of said provided steam so as to achieve a hydrogen:carbon monoxide ratio of at least 2:1.

16. The method according to claim 1, wherein said indirectly heated gasification module is selected from the group consisting of a bubbling fluidized bed type gasification module, a re-circulating fluidized bed type bed gasification module, an entrained bed type gasification module, and a fixed bed type gasification module.

17. The method according to claim 1, further comprising the steps of:

providing at least one surge module.

18. The method according to claim 17, wherein said step of providing said at least one surge module includes at least one of the steps of:

providing a gasification reactor surge module for receiving said synthesis gas and said heat transfer material from said gasification module and for transporting said synthesis gas to said gas conditioning module and for transporting said heat transfer material to said combustion module; and providing an output surge module for receiving said heat transfer material passed from said combustion module through said gas conditioning module for conditioning said gas and for transporting said heat transfer material to said gasification module.

19. A system for gasification with in-situ conditioning, said system comprising:

a gasification module for gasifying a biomass feedstock into a synthesis gas and a condensable material by contacting said biomass feedstock with a thermal transfer material;

a combustion module for contributing to an operation temperature of said gasification module; and a gas conditioning module for receiving said synthesis gas and said condensable material from said gasification module and for conditioning said synthesis gas in an in situ circuit with said gasification module and said combustion module;

wherein said synthesis gas and said condensable material are separated from char and said thermal transfer material;

wherein said char and said transfer material are provided to said combustion module; and wherein said combustion module consumes said char to heat said thermal transfer material and circulates said heated thermal transfer material to said gas conditioning module before said thermal transfer material is circulated to said gasification module.

20. A system for converting a synthesis gas containing hydrocarbons, the system comprising:

an indirectly heated gasification module means for generating a synthesis gas and a condensable material from a carbonaceous fuel, and a combustion module means for contributing to an operation temperature of said gasification module;

in situ gas conditioning module means for receiving said synthesis gas and said condensable material from said gasification module and for operating at said operation temperature to separate said synthesis gas and said condensable material from a catalytically active heat transfer material; and in said gas conditioning module means, means for conditioning said synthesis gas and said condensable material by contact with said catalytically active heat transfer material at said operation temperature to minimize a tar content therein;

wherein said char and said catalytically active heat transfer material are provided to said combustion module means; and wherein said combustion module means consumes said char to contribute to heating said catalytically active heat transfer material and circulates said heat transfer material to said in situ gas conditioning module means before said heat transfer material is circulated to said gasification module means.

21. The system according to claim 20, wherein said means for conditioning said synthesis gas in said gas conditioning module further comprises at least one means for cracking said hydrocarbons and means for shifting said synthesis gas, thereby producing a conditioned gas containing a hydrocarbon:carbon monoxide ratio having a positive hydrogen balance.

22. The system according to claim 21, said system further comprising:
means for providing a steam supply to both said gas conditioning module means and said gasification module means.

23. The system according to claim 21, wherein said shifting said synthesis gas is increased by adjusting an amount of steam input.

24. The system according to claim 21, wherein said means for shifting said synthesis gas is increased by adjusting an amount of steam input so as to achieve a hydrogen:carbon monoxide ratio of at least 2:1.

25. The system according to claim 22, wherein said steam supply is provided to said gasification module in a velocity range of between about 0.50 ft/sec to about 15 ft/sec.

26. The system according to claim 25, wherein said steam supply is provided to said gasification module in a velocity range of between about 0.50 ft/sec to about 10 ft/sec.

27. The system according to claim 20, said system further comprising:
a thermal transfer material containing at least a first portion by weight of said catalytically active heat transfer material; and
means for contacting said thermal transfer material with said synthesis gas in said gas conditioning module thereby enabling said means for conditioning.

28. The system according to claim 27, said system further comprising:
circulating module means for circulating said heat transfer material from said combustion module where said heat transfer material is heated to maintain an operation temperature, to said gas conditioning module where said means for contacting occurs at said operation temperature, and to said gasification module means where said synthesis gas is generated from an input biomass material.

29. The system according to claim 28, wherein said operation temperature is between about 900° C. (1652° F.) to about 1100° C. (2012° F.).

30. The system according to claim 28, said system further comprising:
means for heating said gas conditioning module with heat transfer material from said combustion module thereby maintaining said gas conditioning module at said operation temperature.

31. The system according to claim 27, wherein said catalytically active heat transfer material includes at least one material selected from the group consisting of olivine, calcites, metal oxides, and an iron containing high temperature catalytically active material.

32. The system according to claim 27, wherein said at least a first portion of said catalytically active heat transfer material is between about 50% to 100% by weight.

33. The system according to claim 27, wherein said at least a first potion of said catalytically active heat transfer material is between about 80% to 100% by weight.

34. The system according to claim 27, wherein said at least a first portion of said catalytically active heat transfer material is between about 90% to 100% by weight.

35. The system according to claim 20, wherein said indirectly heated gasification module means is selected from the group consisting of a bubbling fluidized bed type gasification module, a re-circulating fluidized bed type gasification module, an entrained bed type gasification module, and a fixed bed type gasification module.

36. The system according to claim 20, said system further comprising:
at least one surge module means for receiving a volume of material at an input side and for distributing a modified version of said material through an output side.

37. The system according to claim 36, wherein said surge module means is a module selected from the group consisting of:
a gasification reactor surge module means for receiving at said input side said synthesis gas and heat transfer materials from said gasification module and transporting said synthesis gas to said gas conditioning module means and for transporting said heat transfer materials to said combustion module means through said output side; and
an output surge module means for receiving at said input side heat transfer materials passed from said combustion module through said gas conditioning module for conditioning said gas and for transporting said heat transfer material to said gasification module through said output side.

38. An apparatus for treating waste by gasification, said apparatus comprising:
a circulating fluidized bed gasifier module for receiving a heat transfer material from an in situ gas conditioning module and said gas conditioning module receiving a synthesis gas and a condensable material from said gasifier module and for operating at an operation temperature to condition said synthesis gas and said condensable material; and
a combustion module for contributing to said operation temperature of said gasifier module wherein char and a catalytically active heat transfer material are provided to said combustion module; and wherein said combustion module consumes said char to contribute to heating said catalytically active heat transfer material and circulates said heat transfer material to said in situ gas conditioning module before said heat transfer material is circulated to said gasification module;

wherein said gas conditioning module is in a gas communication with each respective said gasifier module and said combustion module, and wherein said gas conditioning module enables an in situ gas conditioning of said synthesis gas and said condensable material by contact with said heat transfer material at said operation temperature to minimize a tar content therein, said in situ conditioning including a cracking reaction and a shifting reaction.

39. An apparatus for conditioning a synthesis gas containing hydrocarbons, said apparatus comprising:
- an indirectly heated gasification module for generating a synthesis gas and a condensable material from a carbonaceous fuel;
- a combustion module for contributing to an operation temperature of said gasification module; and
- an in situ gas conditioning module for receiving said synthesis gas and said condensable material from said gasification module and for operating at said operation temperature to contribute to separating said synthesis gas and said condensable material from char and a catalytically active heat transfer material;

wherein said combustion module consumes said char to heat said heat transfer material and circulates said heat transfer material to said in situ gas conditioning module before said heat transfer material is circulated to said gasification module means; and wherein said conditioning module includes a module for conditioning said synthesis gas and said condensable material by contact with said catalytically active heat transfer material at said operation temperature to minimize a tar content therein, said conditioning module comprising a system for cracking said hydrocarbons and shifting said synthesis gas, thereby producing a conditioned gas containing a hydrogen:carbon monoxide ratio having a positive hydrogen balance.

* * * * *